US011241269B2

United States Patent
Brady et al.

(10) Patent No.: US 11,241,269 B2
(45) Date of Patent: Feb. 8, 2022

(54) SURGICAL DEVICES SWITCHABLE BETWEEN MONOPOLAR FUNCTIONALITY AND BIPOLAR FUNCTIONALITY

(71) Applicant: Ethicon LLC, Guaynabo, PR (US)

(72) Inventors: John Brady, Cincinnati, OH (US); Monica Rivard, Cincinnati, OH (US); Demetrius Harris, Cincinnati, OH (US); Cory Kimball, Cincinnati, OH (US); Matthew Schneider, Blue Ash, OH (US); Chad Frampton, American Fork, UT (US); Richard W. Timm, Cincinnati, OH (US); Michael Ehninger, South Jordan, UT (US)

(73) Assignee: Cilag GmbH International, Zug (CH)

( * ) Notice: Subject to any disclaimer, the term of this patent is extended or adjusted under 35 U.S.C. 154(b) by 301 days.

(21) Appl. No.: 16/375,338

(22) Filed: Apr. 4, 2019

(65) Prior Publication Data
US 2020/0315685 A1    Oct. 8, 2020

(51) Int. Cl.
| | | |
|---|---|---|
| *A61B 18/12* | (2006.01) | |
| *A61B 18/08* | (2006.01) | |
| *A61B 18/14* | (2006.01) | |
| A61B 18/00 | (2006.01) | |

(52) U.S. Cl.
CPC ........ *A61B 18/1206* (2013.01); *A61B 18/085* (2013.01); *A61B 18/1445* (2013.01); *A61B 2018/00601* (2013.01); *A61B 2018/124* (2013.01); *A61B 2018/126* (2013.01); *A61B 2018/1253* (2013.01); *A61B 2018/1412* (2013.01)

(58) Field of Classification Search
CPC .............. A61B 18/1206; A61B 18/085; A61B 18/1445; A61B 2018/1253; A61B 2018/126; A61B 2018/00946; A61B 2018/00952
See application file for complete search history.

(56) References Cited

U.S. PATENT DOCUMENTS

| | | |
|---|---|---|
| 6,068,627 A | 5/2000 | Orszulak et al. |
| 6,277,117 B1 | 8/2001 | Tetzlaff et al. |
| 6,398,779 B1 | 6/2002 | Buysse et al. |
| 6,511,480 B1 | 1/2003 | Tetzlaff et al. |
| 6,743,229 B2 | 6/2004 | Buysse et al. |
| 6,796,981 B2 | 9/2004 | Wham et al. |
| D496,997 S | 10/2004 | Dycus et al. |
| D499,181 S | 11/2004 | Dycus et al. |
| 6,960,210 B2 | 11/2005 | Lands et al. |
| 7,044,949 B2 | 5/2006 | Orszulak et al. |
| D525,361 S | 7/2006 | Hushka |
| 7,101,371 B2 | 9/2006 | Dycus et al. |
| 7,101,372 B2 | 9/2006 | Dycus et al. |

(Continued)

OTHER PUBLICATIONS

"Ligasure(TM) Retractable L-Hook Laparoscopic Sealer/Divider" brochure, Medtronic, 2016 (14 pages).

*Primary Examiner* — Michael F Peffley
(74) *Attorney, Agent, or Firm* — Mintz Levin Cohn Ferris Glovsky and Popeo, P.C.

(57) ABSTRACT

In general, surgical devices switchable between monopolar functionality and bipolar functionality are provided. In an exemplary embodiment, a surgical device is configured to selectively apply each of bipolar energy and monopolar energy.

23 Claims, 8 Drawing Sheets

(56) References Cited

U.S. PATENT DOCUMENTS

| | | |
|---|---|---|
| 7,101,373 B2 | 9/2006 | Dycus et al. |
| 7,112,201 B2 | 9/2006 | Truckai et al. |
| D531,311 S | 10/2006 | Guerra et al. |
| 7,118,587 B2 | 10/2006 | Dycus et al. |
| 7,150,097 B2 | 12/2006 | Sremcich et al. |
| 7,150,749 B2 | 12/2006 | Dycus et al. |
| D535,027 S | 1/2007 | James et al. |
| 7,156,846 B2 | 1/2007 | Dycus et al. |
| 7,169,145 B2 | 1/2007 | Isaacson et al. |
| 7,255,697 B2 | 8/2007 | Dycus et al. |
| 7,267,677 B2 | 9/2007 | Johnson et al. |
| 7,303,557 B2 | 12/2007 | Wham et al. |
| 7,329,256 B2 | 2/2008 | Johnson et al. |
| 7,364,577 B2 | 4/2008 | Wham et al. |
| 7,377,920 B2 | 5/2008 | Buysse et al. |
| 7,384,420 B2 | 6/2008 | Dycus et al. |
| D575,395 S | 8/2008 | Hushka |
| D575,401 S | 8/2008 | Hixson et al. |
| 7,416,101 B2 | 8/2008 | Shelton, IV et al. |
| 7,416,437 B2 | 8/2008 | Sartor et al. |
| 7,445,621 B2 | 11/2008 | Dumbauld et al. |
| 7,473,253 B2 | 1/2009 | Dycus et al. |
| 7,510,556 B2 | 3/2009 | Nguyen et al. |
| 7,553,312 B2 | 6/2009 | Tetzlaff et al. |
| 7,582,087 B2 | 9/2009 | Tetzlaff et al. |
| 7,597,693 B2 | 10/2009 | Garrison |
| 7,641,653 B2 | 1/2010 | Dalla Betta et al. |
| 7,722,607 B2 | 5/2010 | Dumbauld et al. |
| D617,900 S | 6/2010 | Kingsley et al. |
| D618,798 S | 6/2010 | Olson et al. |
| 7,766,910 B2 | 8/2010 | Hixson et al. |
| 7,789,878 B2 | 9/2010 | Dumbauld et al. |
| D627,462 S | 11/2010 | Kingsley |
| 7,846,161 B2 | 12/2010 | Dumbauld et al. |
| 7,947,041 B2 | 5/2011 | Tetzlaff et al. |
| D649,249 S | 11/2011 | Guerra |
| 8,070,748 B2 | 12/2011 | Hixson et al. |
| 8,105,323 B2 | 1/2012 | Buysse et al. |
| 8,241,284 B2 | 8/2012 | Dycus et al. |
| 8,287,528 B2 | 10/2012 | Wham et al. |
| D670,808 S | 11/2012 | Moua et al. |
| 8,323,310 B2 | 12/2012 | Kingsley |
| 8,361,072 B2 | 1/2013 | Dumbauld et al. |
| 8,647,341 B2 | 2/2014 | Dycus et al. |
| 8,668,689 B2 | 3/2014 | Dumbauld et al. |
| RE44,834 E | 4/2014 | Dumbauld et al. |
| 8,968,311 B2 | 3/2015 | Allen, IV et al. |
| D726,910 S | 4/2015 | Lacosta et al. |
| 9,005,200 B2 | 4/2015 | Roy et al. |
| 9,017,372 B2 | 4/2015 | Artale et al. |
| 9,039,691 B2 | 5/2015 | Moua et al. |
| 9,072,524 B2 | 7/2015 | Heard et al. |
| D736,920 S | 8/2015 | Lee et al. |
| D744,100 S | 11/2015 | Chang et al. |
| D744,644 S | 12/2015 | Lee et al. |
| D748,260 S | 1/2016 | Chang et al. |
| 9,232,974 B2 | 1/2016 | Dycus et al. |
| 9,241,759 B2 | 1/2016 | Dycus et al. |
| D750,245 S | 2/2016 | Chang et al. |
| 9,358,028 B2 | 6/2016 | Moua et al. |
| 9,375,263 B2 | 6/2016 | Allen, IV et al. |
| 9,375,270 B2 | 6/2016 | Wham et al. |
| 9,375,271 B2 | 6/2016 | Wham et al. |
| 9,381,060 B2 | 7/2016 | Artale et al. |
| 9,456,863 B2 | 10/2016 | Moua |
| 9,468,491 B2 | 10/2016 | Brandt et al. |
| 9,492,225 B2 | 11/2016 | Dycus et al. |
| 9,498,279 B2 | 11/2016 | Artale et al. |
| D774,190 S | 12/2016 | Lee et al. |
| 9,539,054 B2 | 1/2017 | Peterson et al. |
| 9,549,775 B2 | 1/2017 | Dumbauld et al. |
| 9,592,089 B2 | 3/2017 | Lyons et al. |
| D788,302 S | 5/2017 | O'Neill et al. |
| 9,649,152 B2 | 5/2017 | Moua et al. |
| 9,655,672 B2 | 5/2017 | Artale et al. |
| 9,655,673 B2 | 5/2017 | McCullough, Jr. et al. |
| 9,675,405 B2 | 6/2017 | Trees et al. |
| 9,713,492 B2 | 7/2017 | Garrison et al. |
| 10,010,309 B2 | 7/2018 | Bingham |
| 10,010,366 B2 | 7/2018 | Strobl |
| 2015/0080891 A1* | 3/2015 | Shelton, IV ........ A61B 18/1482 606/48 |
| 2015/0327913 A1* | 11/2015 | Horner ............... A61B 18/1206 606/41 |
| 2017/0135712 A1 | 5/2017 | Boudreaux |
| 2017/0303995 A1* | 10/2017 | Garrison ............ A61B 18/1445 |

\* cited by examiner

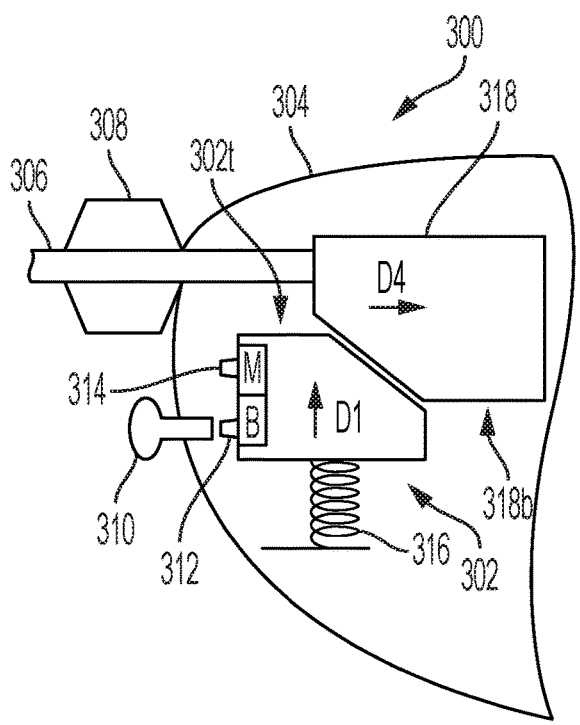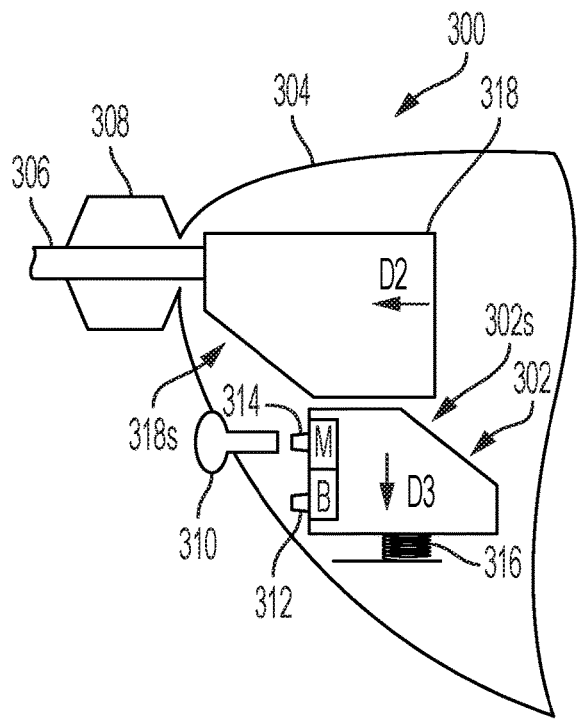
FIG. 13  FIG. 14
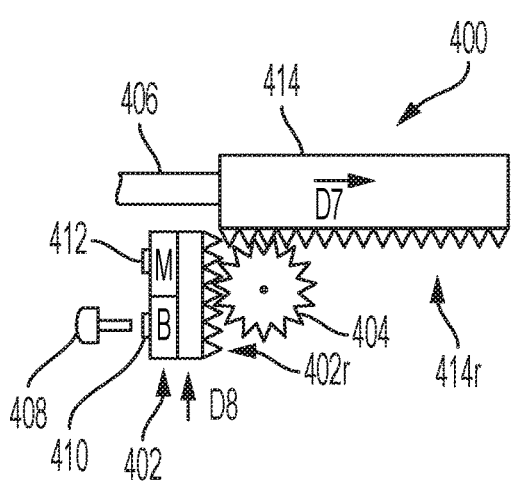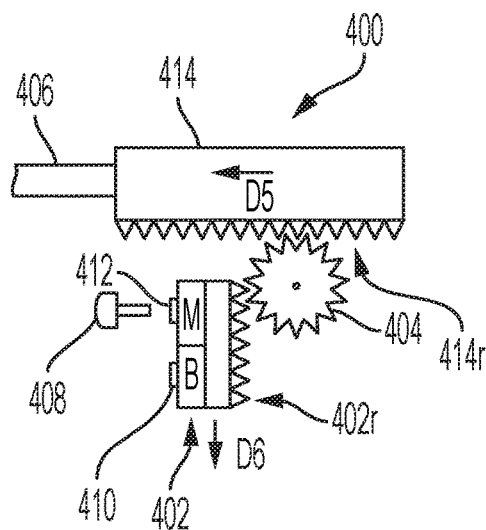
FIG. 15  FIG. 16

SURGICAL DEVICES SWITCHABLE BETWEEN MONOPOLAR FUNCTIONALITY AND BIPOLAR FUNCTIONALITY

FIELD

The present disclosure relates generally to surgical devices switchable between monopolar functionality and bipolar functionality.

BACKGROUND

Various surgical devices can be used for minimally-invasive surgery to compress, transect, and seal different types of tissue. In general, these devices can have an end effector with a pair of opposed jaws that are configured to engage tissue therebetween, and can have a cutting mechanism that is configured to transect tissue engaged by the opposed jaws. The end effector can be configured to apply electrical energy to tissue engaged between the opposed jaws. The application of electrical energy to the engaged tissue can seal and coagulate the tissue, such as to seal tissue being cut by the cutting mechanism to prevent or reduce bleeding.

However, various situations can arise during an operation in which a user wants to apply energy to tissue without having to first grasp tissue between the opposed jaws, such as to selectively apply energy to spots of tissue in a controlled manner without having to clamp and seal an entire section of tissue.

Accordingly, there remains a need for improved energy delivery from surgical devices to tissue.

SUMMARY

In general, surgical devices switchable between monopolar functionality and bipolar functionality are provided.

In one aspect, an electrosurgical device is provided that in one embodiment includes a housing, an elongate shaft extending from the housing and defining a longitudinal axis, and an end effector coupled to a distal end of the elongate shaft. The end effector includes first and second jaws. At least one of the first and second jaws is pivotable relative to the other from an open position, in which the first and second jaws are disposed in spaced relation relative to one another, to a clamping position, in which the first and second jaws cooperate to grasp tissue therebetween. The device also includes a knob configured to rotate relative to the housing to rotate the elongate shaft and end effector. The knob is also configured to longitudinally translate between a first position, in which a pair of electrical contacts are aligned to complete a current path for a bipolar energy circuit allowing the first and second jaws to conduct energy through tissue grasped therebetween, and a second position, in which the pair of electrical contacts are offset to disrupt the current path for the bipolar energy circuit.

The device can have any number of variations. For example, with the knob in the second position, an additional pair of electrical contacts can be aligned to form a current path for a monopolar energy circuit allowing energy to be conducted through the end effector into tissue. In at least some embodiments, the housing can include an upper portion substantially aligned with the longitudinal axis, the housing can include a lower portion with a handle, and the device can further include a first actuation mechanism on the lower portion configured to activate energy delivery to the bipolar energy circuit, and a second actuation mechanism on the upper portion configured to activate energy delivery to the monopolar energy circuit. In at least some embodiments, the handle can include a structure configured to require a user to grasp the device using a pistol grip for actuating the first actuation mechanism with an index finger, and to require a user to grasp the device using a pencil grip for actuating the second actuation mechanism using an index finger.

For another example, the handle can include a structure configured to require a user to grasp the device using a pistol grip for actuating an actuation mechanism with an index finger to selectively conduct bipolar energy through the bipolar energy circuit and monopolar energy through the monopolar energy circuit.

For yet another example, the end effector can include a monopolar shaft having a distal tip positioned adjacent the first and second jaws, and, with the knob in the second position, an additional pair of electrical contacts can be aligned to form a current path for a monopolar energy circuit allowing energy to be conducted through the distal tip of the monopolar shaft and into tissue. In at least some embodiments, distal longitudinal translation of the knob can be configured to advance the monopolar shaft distally relative to the elongate shaft, and proximal longitudinal translation of the knob can be configured to retract the monopolar shaft proximally relative to the elongate shaft.

For still another example, the housing can include a closure trigger configured to move relative to the housing to move at least one of the first and second jaws between the open position and the clamping position.

For another example, longitudinal translation of the knob can be configured to move a switch carriage disposed within the housing between first and second positions, actuation of a button on the housing with the switch carriage in the first position is configured to activate energy delivery to the bipolar energy circuit, and actuation of the button on the housing with the switch carriage in the second position can be configured to activate energy delivery to a monopolar energy circuit allowing energy to be conducted through the end effector into tissue. In at least some embodiments, the switch carriage can include a first contact that aligns with the button when the switch carriage is in the first position, and the switch carriage can include a second contact that aligns with the button when the switch carriage is in the second position.

For still another example, the bipolar energy circuit can include a first positive conductor and a second negative conductor for allowing the first and second jaws to conduct energy through tissue grasped therebetween when the knob is in the first position, and one of the first and second conductors can form a monopolar energy circuit for allowing energy to be conducted through the end effector into tissue when the knob is in the second position. In at least some embodiments, the device can further include a generator configured to detect whether the first positive conductor and the second negative conductor form a closed circuit for bipolar energy delivery or an open circuit for monopolar energy delivery.

In another embodiment an electrosurgical device is provided that includes a housing, an elongate shaft extending from the housing and defining a longitudinal axis, and an end effector coupled to a distal end of the elongate shaft. The end effector is configured to deliver energy to tissue in contact with the end effector. The device also includes a knob configured to rotate relative to the housing to rotate the elongate shaft and end effector. The knob is configured to longitudinally translate in a proximal direction and in a distal direction to selectively switch the device between a bipolar mode, in which the energy is bipolar energy, and a monopolar mode, in which the energy is monopolar energy.

The device can vary in any number of ways. For example, longitudinal translation of the knob in the proximal direction can be configured to cause a first pair of electrical contacts of the surgical device to be operatively connected such that bipolar energy is configured to be delivered to tissue in contact with the end effector, and longitudinal translation of the knob in the distal direction can be configured to cause a second pair of electrical contacts of the surgical device to be operatively connected such that monopolar energy is configured to be delivered to tissue in contact with the end effector. For yet another example, the device can further include a monopolar energy delivery shaft configured to deliver the monopolar energy, to be advanced distally in response to switching the device from the bipolar mode to the monopolar mode, and to be retracted proximally in response to switching the device from the monopolar mode to the bipolar mode, the end effector can include a first jaw with a delivery electrode for delivery of the bipolar energy, and the end effector can include a second jaw with a return electrode for return of the bipolar energy. In at least some embodiments, the monopolar energy delivery shaft can include a distal hook member.

For still another example, the device can further include a positive conductor, the device can further include a negative conductor, in the bipolar mode the positive conductor of the device can be configured to be operatively connected to a positive conductor of a generator and the negative conductor of the device can be configured to be operatively connected to a negative conductor of the generator to allow the generator to deliver energy to the device via the operatively connected positive conductors and to receive energy from the device via the operatively connected negative conductors, and in the monopolar mode the negative conductor of the device can be configured to be operatively connected to the positive conductor of the generator to allow the generator to deliver energy to the device via the operatively connected negative conductor of the device and positive conductor of the generator.

In another aspect, a surgical method is provided that in one embodiment includes positioning an end effector of a surgical device in contact with tissue. The end effector is coupled to a distal end of an elongate shaft of the surgical device. The method also includes rotating a knob of the surgical device to rotate the end effector and the elongate shaft, longitudinally translating the knob in a first direction and thereby causing a pair of electrical contacts of the surgical device to be aligned to complete a current path for a bipolar energy circuit allowing the end effector to conduct energy through the tissue in contact with the end effector, and longitudinally translating the knob in a second direction, which is opposite to the first direction, and thereby causing the pair of electrical contacts of the surgical device to be offset to disrupt the current path.

The method can vary in any number of ways. For example, the method can further include, with the current path completed, causing energy to be conducted through the tissue in contact with the end effector using the pair of electrical contacts, and, with the current path disrupted, causing energy to be conducted through the tissue in contact with the end effector using another pair of electrical contacts of the surgical device. In at least some embodiments, longitudinally translating the knob in the first direction can cause a switch carriage of the surgical device to be in a first position relative to an actuator of the surgical device, causing energy to be conducted with the current path completed can include actuating the actuator, longitudinally translating the knob in the second direction can cause the switch carriage to be in a second position relative to the actuator, and causing energy to be conducted with the current path disrupted can include actuating the actuator. In at least some embodiments, causing energy to be conducted with the current path completed can include actuating a first actuator of the surgical device, and causing energy to be conducted with the current path disrupted can include actuating a second actuator of the surgical device.

For another example, with the pair of electrical contacts aligned, a positive conductor of the surgical device can be operatively connected to a positive conductor of a generator, a negative conductor of the surgical device can be operatively connected to a negative conductor of the generator, and the method can further include causing the generator to deliver energy to the surgical device via the positive conductors of the surgical device and the generator. With the pair of electrical contacts offset, the positive conductor of the surgical device can be disconnected from the positive conductor of the generator, the negative conductor of the surgical device can be operatively connected to the positive conductor of the surgical device, and the method can further include causing the generator to deliver energy to the surgical device via the negative conductor of the surgical device and the positive conductor of the generator.

BRIEF DESCRIPTION OF DRAWINGS

This invention will be more fully understood from the following detailed description taken in conjunction with the accompanying drawings, in which:

FIG. 13 is a side schematic, cross-sectional view of a portion of yet another embodiment of a surgical device;

FIG. 14 is another side schematic, cross-sectional view of a portion of the surgical device of FIG. 13;

FIG. 15 is a side schematic, cross-sectional view of a portion of still another embodiment of a surgical device;

FIG. 16 is another side schematic, cross-sectional view of a portion of the surgical device of FIG. 15;

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, surgical devices switchable between monopolar functionality and bipolar functionality are provided. In an exemplary embodiment, a surgical device is configured to selectively apply each of bipolar energy and monopolar energy. Devices therefore do not need to be switched out during performance of a surgical procedure since the same device can apply each of bipolar energy and monopolar energy any number of times as desired by a surgeon or other medical professional. Additionally, a hospital or other buyer of the surgical device need only purchase a single device, instead of two devices, in order to provide its medical professionals with the ability to apply bipolar energy and monopolar energy, which may reduce overall costs and/or help reduce operating room clutter.

Figure 1:
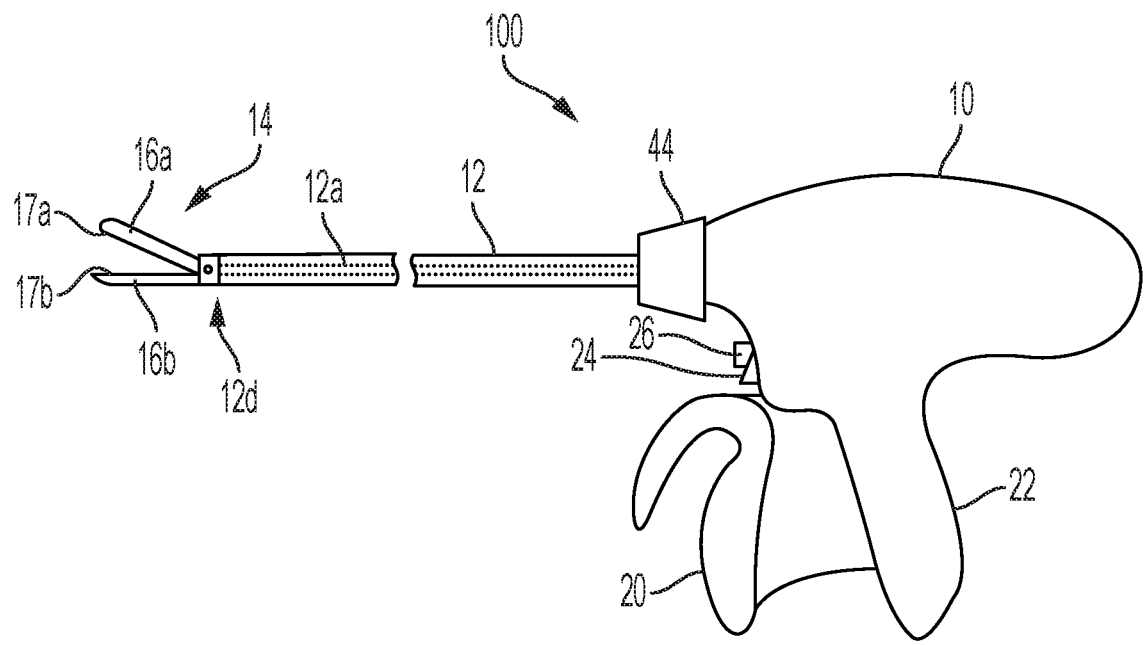
FIG. 1 is a side schematic view of one embodiment of a surgical device.

FIG. 1 illustrates one embodiment of a surgical device configured to grasp and cut tissue. The illustrated surgical device 100 includes a housing 10, an elongate shaft 12, and an end effector 14 configured to grasp tissue. The housing 10 can be any type of pistol-grip, scissor grip, pencil-grip, or other type of handle known in the art that is configured to carry various actuators, such as actuator levers, knobs, triggers, sliders, etc. for actuating various functions such as rotating, articulating, approximating, and/or firing the end effector 14. In the illustrated embodiment, the housing 10 is coupled to a stationary grip handle 22 and a closure grip handle 20 configured to move relative to the stationary grip handle 22 to open and close the end effector 14. The shaft 12 extends distally from the housing 10 and includes at least one lumen 12a extending therethrough for carrying mechanisms for actuating the end effector 14.

The end effector 14 can have a variety of sizes, shapes, and configurations. As shown in FIG. 1, the end effector 14 includes a first, upper jaw 16a and a second, lower jaw 16b disposed at a distal end 12d of the shaft 12. The jaws 16a, 16b are configured to move between an open position, in which the jaws 16a, 16b are spaced a distance apart, and a clamping or closed position, in which the jaws 16a, 16b are moved toward one another and are substantially opposed. The jaws 16a, 16b in the closed position are to engage tissue therebetween and apply a force to tissue disposed therebetween. In the illustrated embodiment, the end effector 14 is configured to move between the open and closed positions by the upper jaw 16a pivoting relative to the shaft 12 and relative to the lower jaw 16b while the lower jaw 16b remains stationary. In other embodiments, both jaws 16a, 16b can be movable to move the end effector 14 between the open and closed positions, or the lower jaw 16b can be configured to pivot relative to the shaft 12 and the upper jaw 16a to move the end effector 14 between the open and closed positions. While the illustrated jaws 16a, 16b have a substantially elongate and straight shape, a person skilled in the art will appreciate that one or both of the jaws 16a, 16b can curve in various directions, such as being curved along a longitudinal length thereof. The jaws 16a, 16b can have any suitable axial length for engaging tissue, and the length can be selected based on the targeted anatomical structure for transection and/or sealing.

The closure handle 20 is configured to pivot relative to and toward and away from stationary handle 22 to move the end effector 14 between the open and closed positions. In particular, the closure handle 20 is movable between a first position and a second position. In the first position, which is illustrated in FIG. 1, the closure handle 20 is offset and spaced apart from the stationary handle 22, and the jaws 16a, 16b of the end effector 14 are open. In at least some embodiments the closure handle 20 is biased to the first position such that the end effector 14 is biased to be open. In the second position the closure handle 20 is positioned adjacent to, or substantially in contact with, the stationary handle 22, and the jaws 16a, 16b of the end effector 14 are closed. Further description of embodiments of end effector opening and closing is provided in U.S. Pat. No. 10,010,309 entitled "Surgical Device With Overload Mechanism" filed Oct. 10, 2014, which is hereby incorporated by reference in its entirety.

In at least some embodiments the device 100 includes a locking feature configured to lock the closure handle 20 in position relative to the stationary handle 22, as will be appreciated by a person skilled in the art. For example, the locking feature can be configured to automatically engage when the closure handle 20 is moved to the second position, e.g., is positioned adjacent to, or substantially in contact with, the stationary handle 22. For another example, the locking feature can be configured to automatically engage at each of a plurality of positions the closure handle 20 is pivoted through between the first and second positions, such as via ratcheting.

The closure handle 20 can use manual or powered components. In manual embodiments the closure handle 20 is configured to be manually moved (e.g., by a user directly or by a user indirectly via robotic surgical control) to manually open/close the end effector 14 using various components, e.g., gear(s), rack(s), drive screw(s), drive nut(s), etc. disposed within the housing 10 and/or shaft 12.

Figure 2:
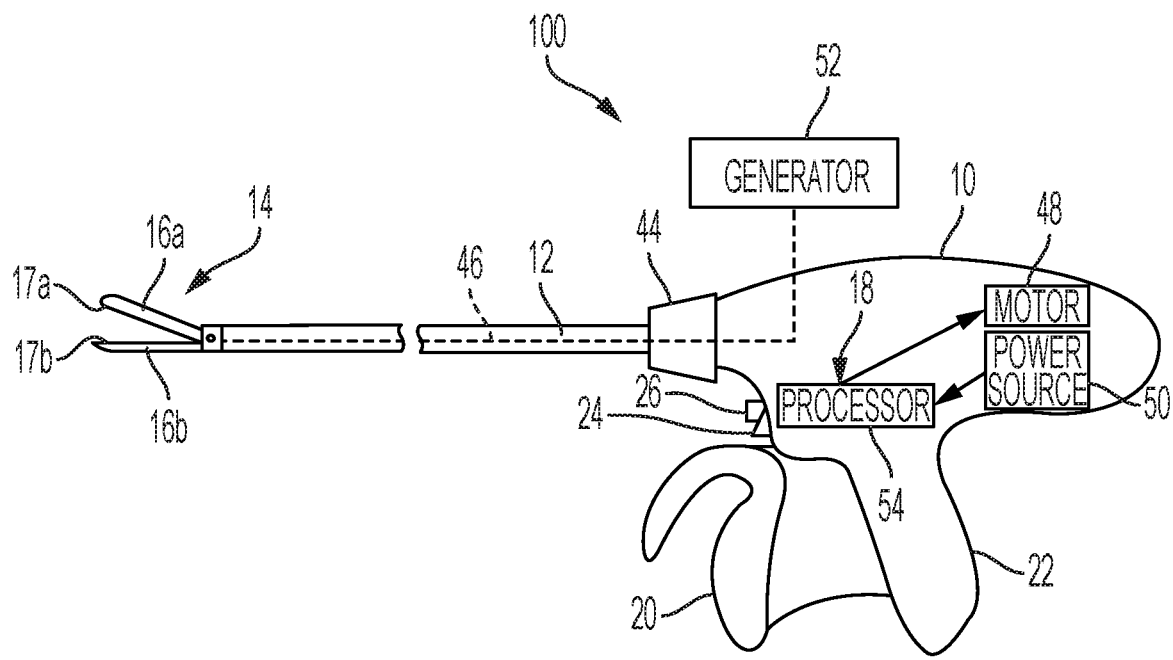
FIG. 2 is a side, partially transparent view of the surgical device of FIG. 1 operatively coupled to a generator.

In powered embodiments, the closure handle 20 is configured to be manually moved (e.g., by a user directly or by a user indirectly via robotic surgical control), thereby causing the end effector 14 to open/close either fully electronically or electronically in addition to manual power. In this illustrated embodiment, as shown in FIG. 2, the device 100 is powered and includes a motor 48, a power source 52, and a processor 54, which in this illustrated embodiment are each disposed in the housing 10. Manual movement of the closure handle 20 is configured to cause the processor 54 to transmit a control signal to be sent to the motor 48, which is configured to interact with various components of the device 100 to cause the jaws 16a, 16b to open/close. The power source 52 is configured to provide on-board power to the processor 54 and the motor 48. In other embodiments, the processor 54 and/or the motor 48 can be configured to be powered instead, or additionally, with an external power source. The device 100 can include one or more sensors to facilitate powered end effector opening and closing and/or other device features, such as tissue cutting. Various embodiments of such sensors are further described in U.S. Pat. No. 7,416,101 entitled "Motor-Driven Surgical Cutting And Fastening Instrument With Loading Force Feedback" filed Jan. 31, 2006 and U.S. Pat. No. 9,675,405 entitled "Methods And Devices For Controlling Motorized Surgical Devices" filed Apr. 8, 2014, which are hereby incorporated by reference in their entireties.

Figure 3:
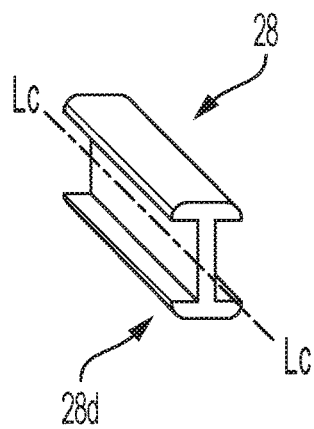
FIG. 3 is a perspective view of a compression member of the surgical device of FIG. 1.

The surgical device 100 includes a cutting or firing actuator 24 configured to be actuated to advance a cutting element to cut tissue grasped between the jaws 16a, 16b. While the actuator 24 can have various configurations, e.g., buttons, knobs, triggers, etc., the illustrated actuator 24 is a button configured to be depressed. The cutting actuator 24 can be in mechanical or electrical communication with various gear(s), rack(s), drive screw(s), drive nut(s), motor (s) (e.g., the motor 48), and/or processor(s) (e.g., the processor 54) to cause the cutting element's movement when the cutting actuator 24 is actuated. The cutting element is configured to transect tissue captured between the jaws 16a, 16b and can be sized and shaped to transect or cut various thicknesses and types of tissue. In one exemplary embodiment, as shown in FIG. 3, an I-beam compression member 28 is configured to travel along a longitudinal axis Lc through slots formed in each jaw 16a, 16b to pull the jaws into a parallel orientation, to compress tissue therebetween, and to transect tissue using a cutting element on the distal end 28d thereof, such as by the distal end 28d having a sharp cutting edge or having a knife blade mounted thereon.

The surgical device 100 includes a sealing actuator 26 configured to be actuated to cause energy, such as radiofrequency (RF) or ultrasound energy, to be applied to tissue engaged by the end effector 14. While the actuator 26 can have various configurations, e.g., buttons, knobs, triggers, etc., the illustrated actuator 26 is a button configured to be depressed. In other embodiments, instead of including a cutting actuator 24 and a sealing actuator 26, a surgical device can include a combined cutting and sealing actuator configured to be actuated to simultaneously cause cutting and sealing.

The device 100 includes various components configured to facilitate the delivering of energy to tissue. These components can be disposed at various locations in the device 100, such as in the proximal handle portion 10 and/or in one or both of the jaws 16a, 16b. Actuating the sealing actuator 26 is configured to cause a signal to be transmitted to the processor 54, which in response is configured to cause delivery of energy from a generator 52 and/or the power source 50 to tissue engaged by the end effector 14. The generator 52 can be incorporated into the handle portion 10 or, as in this illustrated embodiment as shown in FIG. 2, can be a separate unit that is electrically connected to the surgical device 100. The generator 52 is any suitable generator known in the art, such as an RF generator or an ultrasound generator.

The lumen 12a of the shaft 12 has disposed therein one or more electrical paths 46, e.g., leads, conductive members, wires, etc., configured to deliver electrical energy to the end effector 14 in response to actuation of the sealing actuator 26. The one or more electrical paths 46 are operatively coupled to the generator 52 in this illustrated embodiment, with the generator 52 being configured to supply energy to the one or more electrical paths 46. Upon actuation of energy delivery, energy is configured to be delivered to one or more electrodes in one or both of the jaws 16a, 16b via the one or more electrical paths 46 for delivering electrical current to tissue grasped therebetween to effect sealing, marking, cutting, etc. of the tissue. Further description of embodiments of energy application by surgical devices is provided in U.S. Pat. No. 10,010,366 entitled "Surgical Devices And Methods For Tissue Cutting And Sealing" filed Dec. 17, 2014, U.S. Pat. No. 7,169,145 entitled "Tuned Return Electrode With Matching Inductor" filed Nov. 21, 2003, U.S. Pat. No. 7,112,201 entitled "Electrosurgical Instrument And Method Of Use" filed Jan. 22, 2003, and U.S. Patent Pub. No. 2017/0135712 entitled "Methods And Devices For Auto Return Of Articulated End Effectors" filed Nov. 17, 2015, which are hereby incorporated by reference in their entireties.

The device 100 has bipolar functionality in which energy applied to tissue engaged by the end effector 14 is bipolar energy applied by a delivery or active electrode 17a and received by a return electrode 17b. One of the jaws 16a, 16b (the upper jaw 16a in this illustrated embodiment) includes the active electrode 17a on a tissue-facing surface thereof, and the other one of the jaws 16a, 16b (the lower jaw 16b in this illustrated embodiment) includes the return electrode 17b on a tissue-facing surface thereof. The return electrode 17b is electrically isolated from the active electrode 17a such that energy can be applied to tissue grasped between the jaws 16a, 16b from the active electrode 17a and have a return path through the return electrode 17b. The bipolar energy is thus configured to be delivered to tissue grasped between the jaw 16a, 16b when the end effector 14 is in the closed position.

The device 100 also has monopolar functionality in which energy in which energy applied to tissue engaged by the end effector 14 is monopolar energy applied by a monopolar electrode (obscured in FIGS. 1 and 2). An energy return path can be through surrounding tissue, through the device 100 generally, through a ground pad placed on a patient's body, etc. While tissue sealing can be accomplished by applying bipolar energy to tissue grasped by the end effector 14 (e.g., located and clamped between the jaws 16a, 16b), it can be beneficial to apply spot energy to target tissue that is adjacent to the end effector 14 and not grasped thereby (e.g., located outside of the jaws 16a, 16b) to allow for spot coagulation, non-clamping sealing and/or hemostasis, marking tissue, cutting or searing tissue, etc. The device's monopolar functionality allows for this spot energy application. The device 100 thus includes mechanisms for advancing and retracting the monopolar electrode for applying the spot energy. When advanced, at least part of the monopolar electrode protrudes from the end effector 14 to deliver energy to tissue, and when retracted, the monopolar electrode is at least partially withdrawn into the end effector 14 such that at least a portion of the monopolar electrode is protected by the end effector 14.

A surgeon or other medical professional may want to apply each of bipolar energy and monopolar energy during the course of performing a surgical procedure. Bipolar energy can be useful for focused energy application to tissue since the energy is applied to the grasped tissue. Monopolar energy is not as focused since the tissue may serve as the return pole and since the energy is not being applied to tissue located between and being pressed by the end effector's jaws 16a, 16b. Monopolar energy is still useful, however, such as for cutting tissue that the surgeon or other medical professional not does want to bleed, as monopolar energy is configured to be hot enough to provide for coagulation. Traditional surgical devices are often configured to apply only one of bipolar energy or monopolar energy, so time must be taken to switch devices one or more times during the surgical procedure to apply the particular type of energy desired. The device 100 of FIGS. 1 and 2 is configured to selectively apply each of bipolar energy and monopolar energy such that devices do not need to be switched out during performance of a surgical procedure since the same device 100 can apply each of bipolar energy and monopolar energy any number of times as desired by a surgeon or other medical professional. Additionally, a hospital or other buyer of the device 100 need only purchase a single device, instead of two devices, in order to provide its medical professionals with the ability to apply bipolar energy and monopolar energy, which may reduce overall costs and/or help reduce operating room clutter.

In an exemplary embodiment, the device 100 includes a switch mechanism configured to switch the device 100 between a bipolar mode, in which bipolar energy is applied via the bipolar electrodes 17a, 17b in response to actuation of the sealing actuator 26, and a monopolar mode, in which monopolar energy is applied via the monopolar electrode in response to actuation of the sealing actuator 26. The switch mechanism being in a first position corresponds to the device 100 being in the bipolar mode, and the switch mechanism being in a second, different position corresponds to the device 100 being in the monopolar mode. Energy application may thus be achieved via a same actuation mechanism (the sealing actuator 26) regardless of whether the type of energy to be applied is bipolar or monopolar, which may help reduce user error and confusion during the high stress experience of performing a surgical procedure.

Figure 4:
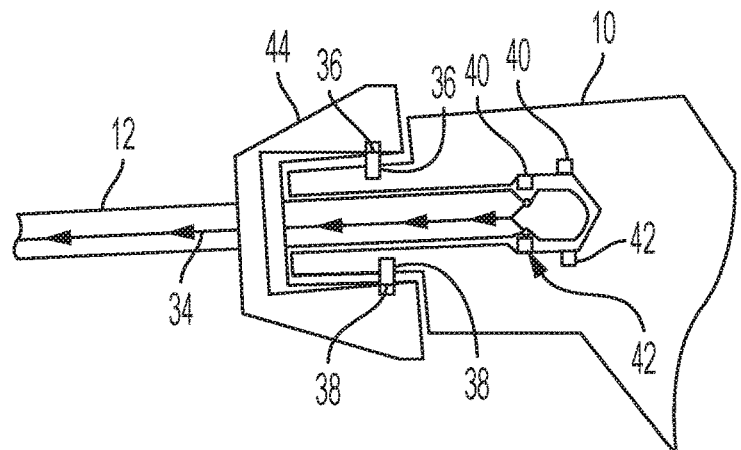
FIG. 4 is a side schematic, cross-sectional view of a portion of the surgical device of FIG. 1.
Figure 5:
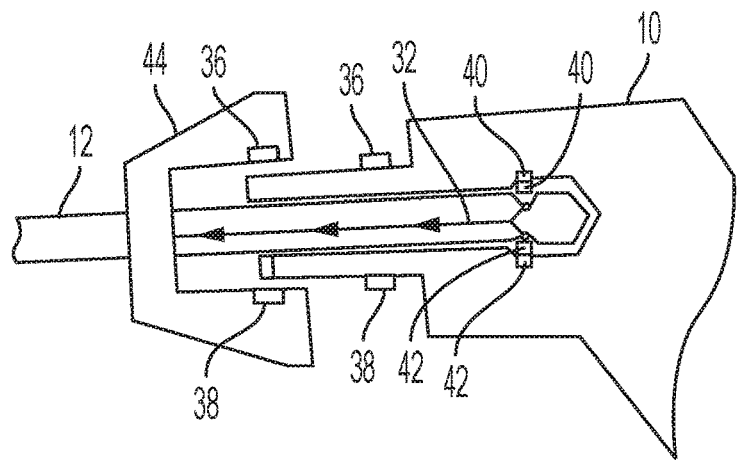
FIG. 5 is another side schematic, cross-sectional view of a portion of the surgical device of FIG. 1.

The switch mechanism can have a variety of configurations. In this illustrated embodiment the switch mechanism is a movable knob 44 configured to move between the first and second positions. The knob 44 is configured to translate longitudinally, e.g., slide linearly, relative to the housing 10 to move between the first and second positions. FIGS. 1, 2, and 4 show the knob 44 in the first position corresponding to bipolar mode. FIG. 5 shows the knob 44 in the second position corresponding to the monopolar mode. As discussed further below, the knob 44 is configured to translate distally to move the device 100 from the bipolar mode to the monopolar mode, and the knob 44 is configured to translate proximally to move the device 100 from the monopolar mode to the bipolar mode. The device 100 can include a first detent (not shown) configured to be engaged when the knob 44 is in the first position to hold the knob 44 in the first position, and/or can include a second detent (not shown) configured to be engaged when the knob 44 is in the second position to hold the knob 44 in the second position. The force applied to the knob 44 to longitudinally translate the knob 44 distally is sufficient to overcome the force of the first detent, and the force applied to the knob 44 to longitudinally translate the knob 44 proximally is sufficient to overcome the force of the second detent.

The knob 44 is also configured to be rotated relative to the housing 10 to cause the shaft 12 and the end effector 14 to rotate about a longitudinal axis of the shaft 12. The knob 44 is thus configured to move in two different ways, translation and rotation, to effectuate two different functions, energy application and shaft/end effector rotation. Surgical devices often include a rotation knob for shaft and end effector rotation, so using the knob in connection with energy application as discussed herein may facilitate easy and/or cost effective incorporation of a switch mechanism into existing device designs.

The device 100 includes at least two pairs of electrical contacts configured to facilitate selective operation of the device 100 in the bipolar and monopolar modes. When the knob 44 is in the first position and the device 100 is in the bipolar mode, a first pair of the electrical contacts is configured to be in electric communication with one another and a second pair of the electrical contacts is configured to not be in electric communication with one another. Conversely, when the knob 44 is in the second position and the device 100 is in the monopolar mode, the first pair of the electrical contacts is configured to not be in electric communication with one another and the second pair of the electrical contacts is configured to be in electric communication with one another. Accordingly, which electrical contacts are in communication with one another defines which type of energy (bipolar or monopolar) the device 100 is configured to deliver in response to actuation of the sealing actuator 26.

As shown in FIGS. 4 and 5, the device 100 in this illustrated embodiment includes four pairs of electrical contacts 36, 38, 40, 42. Two pairs of electrical contacts 36, 38 are associated with the bipolar mode, and two other pairs of electrical contacts 40, 42 are associated with the monopolar mode. The bipolar-associated electrical contacts 36, 38 are located distal to the monopolar-associated electrical contacts 40, 42.

FIG. 4 shows the bipolar-associated electrical contacts 36, 38 in electric communication with one another to form a current path 34 for a bipolar energy circuit to provide for bipolar energy delivery through the end effector 14, as discussed further below. The monopolar-associated electrical contacts 40, 42 are not in electric communication with one another, and a current path 32 for a monopolar energy circuit is disabled or inactive. When the knob 44 is translated distally from its first position (FIG. 4) to its second position (FIG. 5), the bipolar-associated electrical contacts 36, 38 move out of electric contact with one another since half of each of the pairs 36, 38 moves distally with the knob 44, and the monopolar-associated electrical contacts 40, 42 move into electric contact with one another since half of each of the pairs 340, 42 moves distally with the knob 44. FIG. 5 shows the monopolar-associated electrical contacts 40, 42 in electric communication with one another to form the current path 32 for the monopolar energy circuit to provide for monopolar energy delivery through the end effector 14. The bipolar-associated electrical contacts 36, 38 are not in electric communication with one another, and the current path 34 for the bipolar energy circuit is disabled or inactive. When the knob 44 is translated proximally from its second position (FIG. 5) to its first position (FIG. 4), the bipolar-associated electrical contacts 36, 38 move into electric contact with one another since half of each of the pairs 36, 38 moves proximally with the knob 44, and the monopolar-associated electrical contacts 40, 42 move out of electric contact with one another since half of each of the pairs 40, 42 moves proximally with the knob 44. Thus, only one of the monopolar energy circuit and the bipolar energy circuit can be active at a time.

Figure 6:
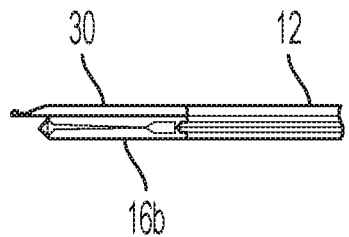
FIG. 6 is a side view of a distal portion of the surgical device of FIG. 1 with a monopolar shaft thereof in an extended position.
Figure 7:
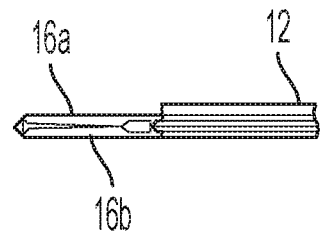
FIG. 7 is a side view of a distal portion of the surgical device of FIG. 1 with the monopolar shaft thereof in a retracted position.

The longitudinal movement of the knob 44 can also be configured to cause selective advancement and retraction of a monopolar shaft 30 of the device 100 configured apply the monopolar energy. The monopolar electrode is located at a distal tip 30d of the monopolar shaft 30. FIG. 6 corresponds to the knob 44 position in FIG. 5 and illustrates the monopolar shaft 30, including its distal tip 30d, distally advanced from the shaft 12. A longitudinal length of the monopolar shaft 30 that extends distally from the shaft 12 corresponds to the longitudinal distance that the knob 44 moves to move from its first position to its second position. FIG. 7 corresponds to the knob 44 position in FIG. 4 and illustrates the monopolar shaft 30, including its distal tip 30d, disposed in the shaft 12. In other embodiments, the monopolar shaft 30 may not be fully retracted into the shaft 12 when the knob 44 is in its first position. In still other embodiments, the monopolar shaft 30 can be fixed in the extended position and be configured to not extend or retract, e.g., longitudinally translate proximally or distally, in response to the knob's longitudinal translation.

In other embodiments, the device 100 can include only one of the bipolar-associated pairs of electrical contacts 36, 38 and/or only one of the monopolar-associated electrical contacts 40, 42. In still other embodiments, the device 100 can include at least one pair of bipolar-associated pairs of electrical contacts in addition to the bipolar-associated pairs of electrical contacts 36, 38 and/or at least one pair of monopolar-associated pairs of electrical contacts in addition to the monopolar-associated electrical contacts 40, 42.

Figure 8:
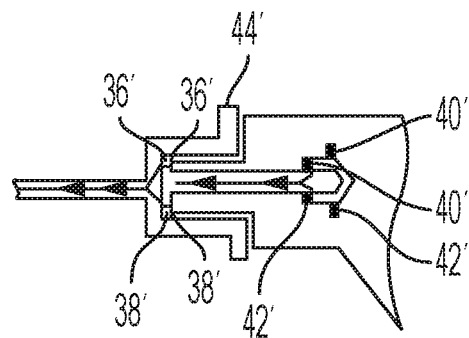
FIG. 8 is a side schematic, cross-sectional view of a portion of another embodiment of a surgical device.
Figure 9:
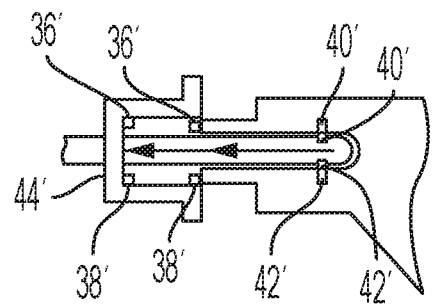
FIG. 9 is another side schematic, cross-sectional view of a portion of the surgical device of FIG. 8.

FIGS. 8 and 9 illustrate an alternate embodiment where two pairs of electrical contacts 36', 38' are associated with the bipolar mode, and two other pairs of electrical contacts 40', 42' are associated with the monopolar mode. The monopolar-associated electrical contacts 40', 42' are in a same location as the monopolar-associated electrical contacts 40, 42 of FIGS. 4 and 5, and the bipolar-associated electrical contacts 36', 38' are still located distal to the monopolar-associated electrical contacts 40', 42'. However, the bipolar-associated electrical contacts 36', 38' in this illustrated embodiment are located differently than the bipolar-associated electrical contacts 36, 38 of FIGS. 4 and 5. Instead of having the point of contact be vertically facing like the bipolar-associated electrical contacts 36, 38 of FIGS. 4 and 5, the point of contact for the bipolar-associated electrical contacts 36', 38' of FIGS. 8 and 9 is horizontally-facing, where the horizontal direction is defined by the proximal and distal directions. FIGS. 8 and 9 also illustrate an alternate shape for a movable knob 44' otherwise configured and used similar to the movable knob 44.

In other embodiments, the device can include only one of the bipolar-associated pairs of electrical contacts 36', 38' and/or only one of the monopolar-associated electrical contacts 40', 42'. In still other embodiments, the device can include at least one pair of bipolar-associated pairs of electrical contacts in addition to the bipolar-associated pairs of electrical contacts 36', 38' and/or at least one pair of monopolar-associated pairs of electrical contacts in addition to the monopolar-associated electrical contacts 40', 42'.

Referring again to the device 100 of FIGS. 1 and 2, the device 100 includes a mode sensor 18 configured to recognize whether the device 100 is in bipolar mode or monopolar mode, e.g., whether the first pair of the electrical contacts are in electric communication with one another (bipolar mode) or whether the second pair of the electrical contacts are in electric communication with one another (monopolar mode). The mode sensor 18 can have any of a variety of configurations, such as a pressure sensor configured to monitor whether or not a proximal side of the knob 44 is pushed against the housing 10, a location sensor configured to sense whether the knob 44 is located in the first position or the second position, a switch configured to be engaged when the knob 44 is in one of the first and second positions and disengaged when the knob 44 is in the other of the first and second positions, etc. The mode sensor 18 is operatively coupled to the processor 54 and is configured to provide a signal thereto indicative of its monitored parameter(s). The processor 54 is configured to direct energy, e.g., from the generator 52, to the active one of the current path 34 for the bipolar energy circuit and the current path 32 for the monopolar energy circuit.

The device 100 of FIGS. 1 and 2 is configured to be grasped by a user using a pistol grip to allow for actuation of each of the closure trigger 20, the cutting actuator 24, and the sealing actuator 26. The user may therefore grip the device 100 in the same way for end effector opening/closing, tissue cutting, bipolar energy application, and monopolar energy application, which may help reduce user hand fatigue. In other embodiments, a surgical device configured to switch between bipolar and monopolar modes can be configured to be grasped by a user using a pistol grip for effecting one or more functions of the device and using a pencil grip for effecting one or more other functions of the device. Requiring the user to switch between the pistol grip and the pencil grip to actuate various different functions of the device may help ensure that functions are not accidentally actuated since one or more functions cannot be actuated easily, if at all, using a pencil grip while another one or more functions cannot be actuated easily, if at all, using a pistol grip.

Figure 10:
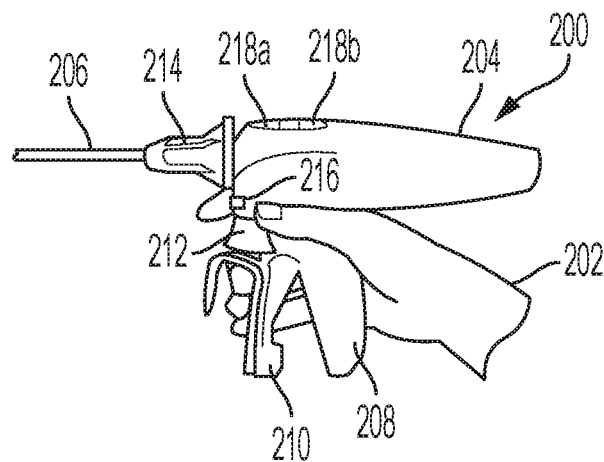
FIG. 10 is a side view of another embodiment of a surgical device being held by hand.
Figure 11:
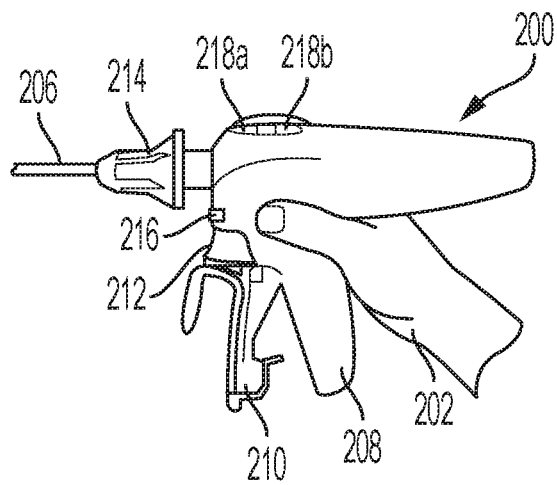
FIG. 11 is a side view of the surgical device of FIG. 10 being held in another way by hand.
Figure 12:
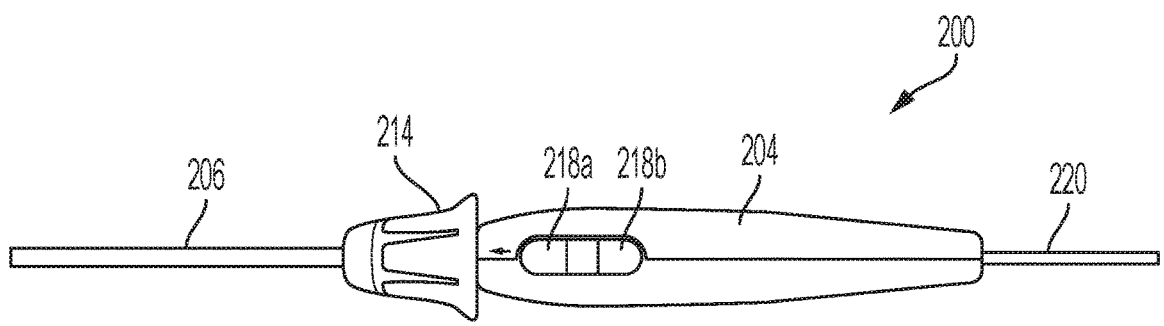
FIG. 12 is a top view of the surgical device of FIG. 10.

FIGS. 10-12 illustrate one embodiment of a surgical device 200 configured to switch between bipolar and monopolar modes can be configured to be grasped by a user using a pistol grip for effecting one or more functions of the device and using a pencil grip for effecting one or more other functions of the device. FIG. 10 illustrates a user's hand 202 grasping the device 200 using a pistol grip, FIG. 11 illustrates the user's hand 202 grasping the device 200 using a pencil grip, and FIG. 12 is a top view of the device 200 without showing the user's hand 202.

Figure 10A:
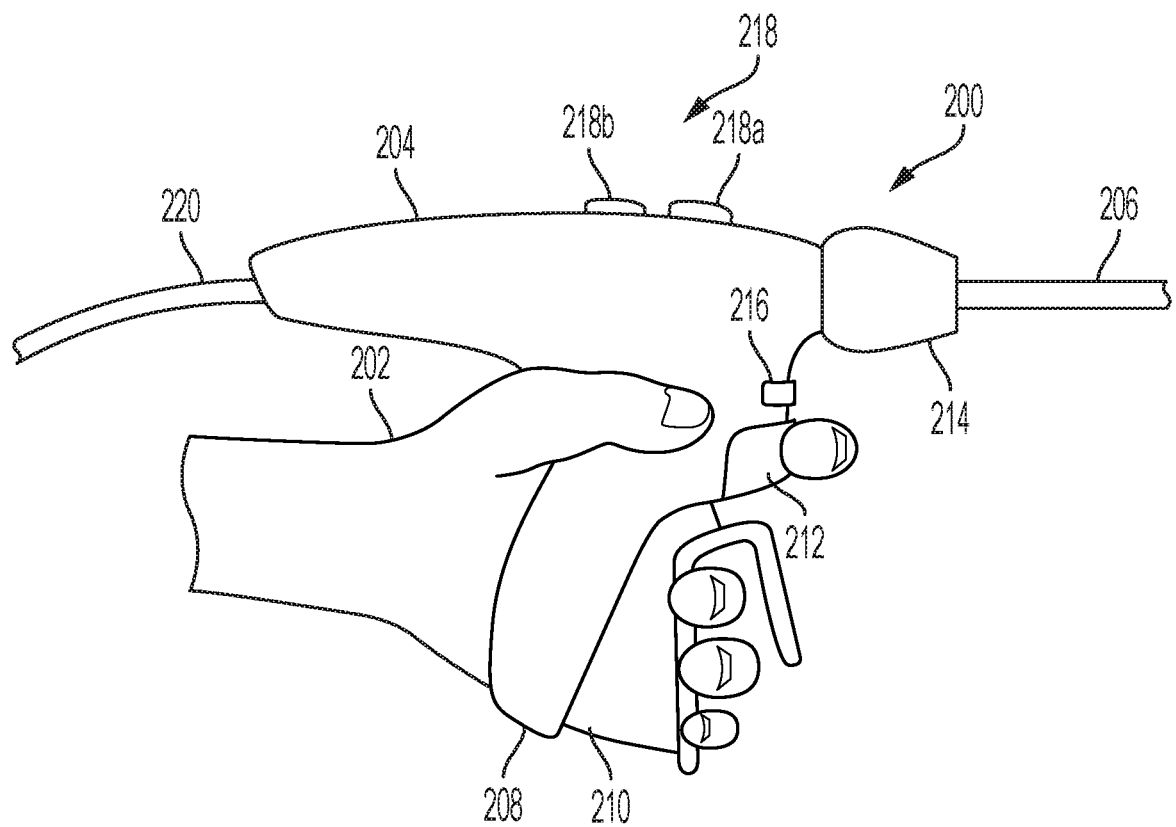
FIG. 10A is a side schematic view of the surgical device of FIG. 10 being held by hand.
Figure 11A:
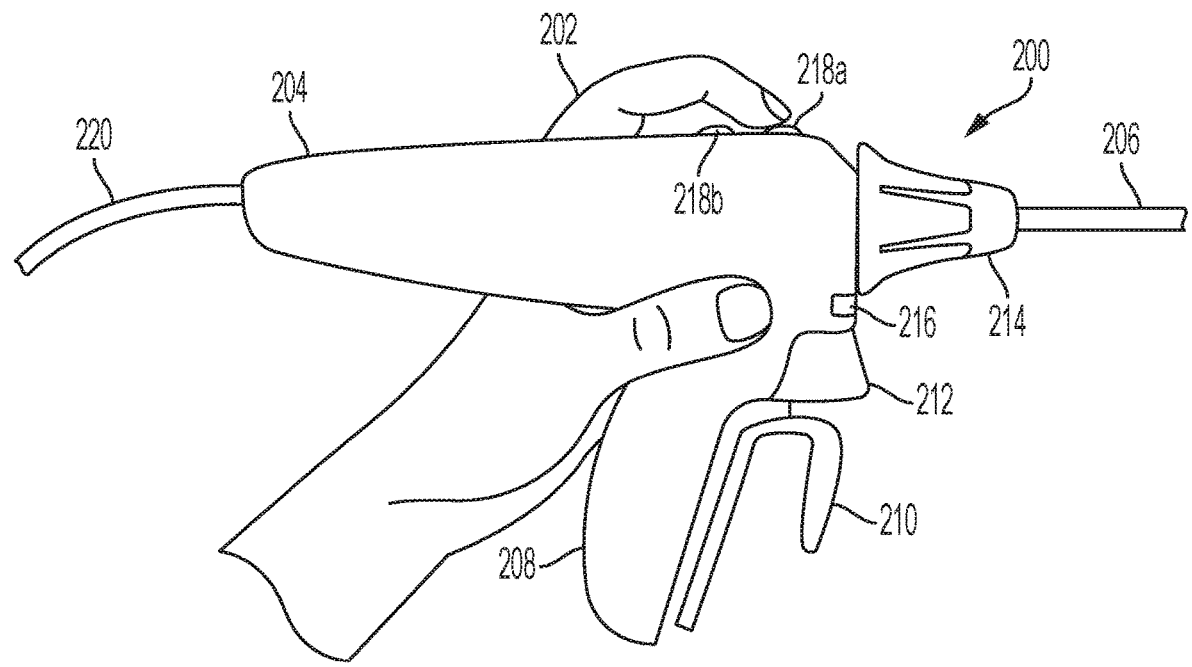
FIG. 11A is a side schematic view of the surgical device of FIG. 11 being held by hand.

The surgical device 200 of FIGS. 10-12 is generally configured and used similar to the device 100 of FIG. 1 and includes a housing 204, an elongate shaft 206, an end effector (not shown) disposed at a distal end of the shaft 206, a stationary grip handle 208, a closure grip handle 210 that can use manual or powered components, a cutting or firing actuator 212, a movable knob 214, a mode sensor (not shown), one or more electrical paths (not shown), a delivery or active electrode (not shown), a return electrode (not shown), a monopolar shaft (not shown), a monopolar electrode (not shown), and at least two pairs of electrical contacts (not shown). In powered embodiments, the device 200 can include a motor, a power source, and a processor, and can be configured to operatively couple to a generator. FIGS. 10A, 11A, and 12 show a cord 220 extending from the device 200 toward operative coupling with a generator (not shown).

In this illustrated embodiment the device 100 includes a bipolar energy actuator 216 and a monopolar energy actuator 218. The monopolar energy actuator 218 includes a first actuator 218a configured to be actuated to apply monopolar energy for cutting tissue, and includes a second actuator 218b configured to be actuated to apply monopolar energy for coagulating tissue. The first and second actuators can have different shapes, sizes, and/or colors to help distinguish their functionality, such as different colors with yellow for the first actuator 218a and blue for the second actuator 218b.

The bipolar energy actuator 216 is located similar to the sealing actuator 26 of FIGS. 1 and 2 and is similarly configured to be actuated by an index finger of the user's hand 202 when the user is grasping the device 200 using a pistol grip, as shown in FIGS. 10 and 10A. FIGS. 10 and 10A also show the knob 214 in the first position corresponding to bipolar mode. The monopolar energy actuator 218 is located on a top of the housing 204 and is configured to be actuated by an index finger of the user's hand 202 when the user is grasping the device 200 using a pencil grip, as shown in FIGS. 11 and 11A. FIGS. 11 and 11A also show the knob 214 in the second position corresponding to monopolar mode. The device 100 being configured to encourage, if not require, the user to have different grips of the device 200 for bipolar energy application (pistol grip) and monopolar energy application (pencil grip) may help ensure that the desired type of energy is applied.

As discussed above, a surgical device configured to switch between bipolar and monopolar modes can include a mode sensor configured to recognize whether the device is in bipolar mode for bipolar energy delivery or monopolar mode for monopolar energy delivery. In other embodiments, instead of including a mode sensor, a surgical device configured to switch between bipolar and monopolar modes can include a switch carriage configured to enable only one of a bipolar energy circuit (bipolar mode) and a monopolar energy circuit (monopolar mode) at a time. In this way, the energy mode of the device, either bipolar mode or monopolar mode, can be mechanically controlled, e.g., using the switch carriage, instead of electronically controlled, e.g., using the mode sensor. Such a device may thus have less power and/or processing requirements than a device including a mode sensor.

FIGS. 13 and 14 illustrate one embodiment of a surgical device 300 configured to switch between bipolar and monopolar modes and that includes a switch carriage 302. The surgical device 300 of FIGS. 13 and 14 is generally configured and used similar to the device 100 of FIG. 1 and includes a housing 304 having the switch carriage 302 disposed therein, an elongate shaft 306, an end effector (not shown) disposed at a distal end of the shaft 306, a stationary grip handle (not shown), a closure grip handle (not shown) that can use manual or powered components, a cutting or firing actuator (not shown), a movable knob 308, a sealing actuator 310, one or more electrical paths (not shown), a delivery or active electrode (not shown), a return electrode (not shown), a monopolar shaft (not shown), a monopolar electrode (not shown), and at least two pairs of electrical contacts (not shown). In powered embodiments, the device 300 can include a motor, a power source, and a processor, and can be configured to operatively couple to a generator. The sealing actuator 310 in this illustrated embodiment is a depressible button.

The movable knob 308 is operatively coupled to the switch carriage 302 such that the longitudinal movement of the movable knob 308 to move the device 300 between bipolar and monopolar modes causes movement of the switch carriage 302. The switch carriage 302 is configured to move between a first position (shown in FIG. 13), corresponding to bipolar mode, and a second position (shown in FIG. 14), corresponding to monopolar mode, in response to movement of the movable knob 308.

The first position of the switch carriage 302 corresponds to a first position of the movable knob 308 and to the device 300 being in bipolar mode. When the switch carriage 302 is in the first position, the sealing actuator 310 is aligned with a first switch 312 of the switch carriage 302 and is misaligned from a second switch 314 of the switch carriage 302. Thus, when the switch carriage 302 is in the first position and the sealing actuator 310 is actuated, e.g., the button is depressed, the sealing actuator 310 is pushed to contact and engage the first switch 312. The first switch 312 includes an electrical contact included in the device's bipolar energy circuit such that when the first switch 312 is engaged, the bipolar energy circuit is active and bipolar energy can be delivered by the end effector, e.g., by the active electrode located at the end effector. The second switch 314 of the switch carriage 302 is disengaged when the switch carriage 302 is in the first position such that the device's monopolar energy circuit is inactive or disabled.

The second position of the switch carriage 302 corresponds to a second position of the movable knob 308 and to the device 300 being in monopolar mode. When the switch carriage 302 is in the second position, the sealing actuator 310 is aligned with the second switch 314 of the switch carriage 302 and is misaligned from the first switch 312 of the switch carriage 302. Thus, when the switch carriage 302 is in the second position and the sealing actuator 310 is actuated, e.g., the button is depressed, the sealing actuator 310 is pushed to contact and engage the second switch 314. The second switch 314 includes an electrical contact included in the device's monopolar energy circuit such that when the second switch 314 is engaged, the monopolar energy circuit is active and monopolar energy can be delivered by the end effector, e.g., by the monopolar electrode. The first switch 312 of the switch carriage 302 is disengaged when the switch carriage 302 is in the second position such that the device's bipolar energy circuit is inactive or disabled.

The switch carriage 302 is operatively coupled to a compressible member 316 configured to facilitate the movement of the switch carriage 302 between its first and second positions. The compressible member 316 is a coil spring in this illustrated embodiment but can have other configurations, such as another type of spring (e.g., a volute spring, a leaf spring, etc.), an elastic member similar to a rubber band, a foam block, etc. The compressible member 316 is configured to move between an expanded configuration, shown in FIG. 13, and a compressed configuration, shown in FIG. 14. The compressible member 316 is biased to the expanded configuration.

When the movable knob 308 and the switch carriage 302 are in their respective first positions, the compressible member 316 is configured to urge the switch carriage 302 in an upward direction D1 toward the shaft 306 and toward a block member 318 disposed within the housing 302 and at a proximal end of the shaft 306. The block member 318 is urged upward with a proximal-facing sloped surface 302s of the switch carriage 302 abutting a distal-facing sloped surface 318s of the block member 318. The abutment of the sloped surfaces 302s, 318s, ensures that the switch carriage 302 is in a proper vertical position for the first switch 312 to be aligned with the sealing actuator 310 when the knob 308 is in its first position corresponding to bipolar mode.

When the movable knob 308 is moved in a distal direction D2 to move from its first position to its second position, the shaft 302 and block member 318 also move distally. The distal movement of the block member 318 causes the sloped surface 318s of the block member 318 to slide along the sloped surface 302s of the switch carriage 302 similar to a ramp, which moves the switch carriage 302 in a downward direction D3 and causes compression of the compressible member 316. When the knob 308 has been fully moved to its second position, as shown in FIG. 14, the block member 318 has moved distally enough for the block member's sloped surface to pass and disengage from the sloped surface 302s of the switch carriage 302 and for a bottom surface 318b of the block member 318 to face and abut a top surface 302t of the switch carriage 302. The abutment of the top and bottom surfaces 302t, 318b ensures that the switch carriage 302 is in a proper vertical position for the second switch 314 to be aligned with the sealing actuator 310 when the knob 308 is in its second position corresponding to monopolar mode.

When the movable knob 308 is moved in a proximal direction D4 to move from its second position to its first position, the shaft 302 and block member 318 also move proximally. The proximal movement of the block member 318 causes the bottom surface 318b of the block member 318 to slide along the top surface 302t of the switch carriage 302 until the block member 318 has been moved proximally enough relative to the switch carriage 302 for the sloped surfaces 302s, 318s to abut and be engaged. Continued proximal movement of the block member 318 causes the sloped surface 318s of the block member 318 to slide along the sloped surface 302s of the switch carriage 302 similar to a ramp, which moves the switch carriage 302 in the upward direction D1 and causes expansion of the compressible member 316. When the knob 308 has been fully moved to its first position, as shown in FIG. 13, the switch carriage 302 is in a proper vertical position for the first switch 312 to be aligned with the sealing actuator 310.

FIGS. 15 and 16 illustrate another embodiment of a surgical device 400 configured to switch between bipolar and monopolar modes and that includes a switch carriage 402. In this illustrated embodiment, the device 400 includes a gear 404 configured to facilitate movement of the switch carriage 402 between a first position (shown in FIG. 15), corresponding to bipolar mode, and a second position (shown in FIG. 16), corresponding to monopolar mode, in response to movement of the device's movable knob (not shown).

The surgical device 400 of FIGS. 15 and 16 is generally configured and used similar to the device 100 of FIG. 1 and includes a housing (not shown) having the switch carriage 402 disposed therein, an elongate shaft 406, an end effector (not shown) disposed at a distal end of the shaft 406, a stationary grip handle (not shown), a closure grip handle (not shown) that can use manual or powered components, a cutting or firing actuator (not shown), a movable knob (not shown), a sealing actuator 408, one or more electrical paths (not shown), a delivery or active electrode (not shown), a return electrode (not shown), a monopolar shaft (not shown), a monopolar electrode (not shown), and at least two pairs of electrical contacts (not shown). In powered embodiments, the device 400 can include a motor, a power source, and a processor, and can be configured to operatively couple to a generator. The sealing actuator 408 in this illustrated embodiment is a depressible button.

The first position of the switch carriage 402 corresponds to a first position of the movable knob and to the device 400 being in bipolar mode. When the switch carriage 402 is in the first position, the sealing actuator 408 is aligned with a first switch 410 of the switch carriage 402 and is misaligned from a second switch 412 of the switch carriage 402. Thus, when the switch carriage 402 is in the first position and the sealing actuator 408 is actuated, e.g., the button is depressed, the sealing actuator 408 is pushed to contact and engage the first switch 410. The first switch 410 includes an electrical contact included in the device's bipolar energy circuit such that when the first switch 410 is engaged, the bipolar energy circuit is active and bipolar energy can be delivered by the end effector, e.g., by the active electrode located at the end effector. The second switch 412 of the switch carriage 402 is disengaged when the switch carriage 402 is in the first position such that the device's monopolar energy circuit is inactive or disabled.

The second position of the switch carriage 402 corresponds to a second position of the movable knob and to the device 400 being in monopolar mode. When the switch carriage 402 is in the second position, the sealing actuator 408 is aligned with the second switch 412 of the switch carriage 402 and is misaligned from the first switch 410 of the switch carriage 402. Thus, when the switch carriage 402 is in the second position and the sealing actuator 408 is actuated, e.g., the button is depressed, the sealing actuator 408 is pushed to contact and engage the second switch 412. The second switch 412 includes an electrical contact included in the device's monopolar energy circuit such that when the second switch 412 is engaged, the monopolar energy circuit is active and monopolar energy can be delivered by the end effector, e.g., by the monopolar electrode. The first switch 410 of the switch carriage 302 is disengaged when the switch carriage 402 is in the second position such that the device's bipolar energy circuit is inactive or disabled.

The switch carriage 402 is operatively coupled to the gear 404, which is configured to facilitate movement of the switch carriage 402 between its first and second positions. The switch carriage 402 includes a toothed rack 402r engaged with teeth of the gear 404. The teeth of the gear 404 are also engaged with a toothed rack 414r of a block member 414 at a proximal end of the shaft 406.

When the movable knob is moved in a distal direction D5 to move from its first position to its second position, the shaft 406 and the block member 414 also move distally. The distal movement of the block member 414 causes the gear 404 to rotate (counterclockwise in this illustrated embodiment) due to the engagement of the gear 404 with the block member's toothed rack 414r. The rotation of the gear 404 causes the switch carriage 402 to move in a downward direction D6 due to the engagement of the gear 404 with the switch carriage's toothed rack 402r. When the knob has been fully moved to its second position, as shown in FIG. 16, the gear 404 has rotated enough to cause enough movement of the switch carriage 402 for the second switch 412 to be aligned with the sealing actuator 408. The switch carriage 402 is thus in a proper vertical position for the monopolar energy circuit to be activated in response to the sealing actuator 408 being actuated and engaging the second switch 412.

When the movable knob is moved in a proximal direction D7 to move from its second position to its first position, the shaft 406 and the block member 414 also move proximally. The proximal movement of the block member 414 causes the gear 404 to rotate (clockwise in this illustrated embodiment) due to the engagement of the gear 404 with the block member's toothed rack 414r. The rotation of the gear 404 causes the switch carriage 402 to move in an upward direction D8 due to the engagement of the gear 404 with the switch carriage's toothed rack 402r. When the knob has been fully moved to its first position, as shown in FIG. 15, the gear 404 has rotated enough to cause enough movement of the switch carriage 402 for the first switch 410 to be aligned with the sealing actuator 408. The switch carriage 402 is thus in a proper vertical position for the bipolar energy circuit to be activated in response to the sealing actuator 408 being actuated and engaging the first switch 410.

As discussed above, a surgical device configured to switch between bipolar and monopolar modes can include a switch carriage configured to enable only one of a bipolar energy circuit (bipolar mode) and a monopolar energy circuit (monopolar mode) at a time. In other embodiments, instead of including a switch carriage, a surgical device configured to switch between bipolar and monopolar modes and to enable only one of a bipolar energy circuit and a monopolar energy circuit at a time can include a positive conductor or terminal and a negative conductor or terminal configured to enable only one of a bipolar energy circuit (bipolar mode) and a monopolar energy circuit (monopolar mode) at a time.

In an exemplary embodiment, the positive and negative terminals are located on a monopolar shaft of the surgical device that is configured to be advanced and retracted, e.g., via movement of the device's movable knob as discussed above. Depending on whether the monopolar shaft is in its advanced position or its retracted position, the positive terminal is either active or inactive. When the monopolar shaft is in its retracted portion, the positive terminal is active or enabled so as to activate the device's bipolar energy circuit and allow bipolar energy to be applied by the device. With the positive terminal active, the device's monopolar energy circuit is inactive or disabled such that monopolar energy cannot be applied. When the monopolar shaft is in its advanced portion, the positive terminal is inactive so as to activate the device's monopolar energy circuit and allow monopolar energy to be applied by the device. With the positive terminal inactive, the device's bipolar energy circuit is inactive or disabled such that bipolar energy cannot be applied.

A surgical device including positive and negative terminals as discussed herein may take advantage of a generator's existing functionality to facilitate switching between the monopolar and bipolar modes. A generator configured to be operatively coupled to a surgical device to provide energy thereto for delivery to tissue by the device often includes a positive conductor or terminal, a negative conductor or terminal, and a ground terminal. The device's positive terminal is configured to either be engaged with one of the generator's positive terminal and negative terminal depending on whether the monopolar shaft is in its advanced position or its retracted position. The device's negative terminal is configured to either be disengaged from the generator or to be engaged with the generator's negative terminal depending on whether the monopolar shaft is in its advanced position or its retracted position. Based on which of the device's terminals and engaged with one or two of the generator's terminals, the generator can either delivery bipolar energy or monopolar energy.

The generator is configured to use impedance to detect the device's positive terminal being engaged or not with the generator's positive terminal and the device's negative terminal being engaged or not with the generator's negative terminal. When the monopolar shaft is in its retracted portion, the device's positive terminal is engaged with the generator's positive terminal and the device's negative terminal is engaged with the generator's negative terminal, thereby allowing the generator to delivery bipolar energy to the device for delivery to tissue. A low impedance, e.g., less than about 10 Ohms, detected by the generator is indicative of a closed circuit state in which the device's positive terminal is engaged with the generator's positive terminal and the device's negative terminal is engaged with the generator's negative terminal. In the closed circuit state, the generator is configured to send current via its positive terminal to provide bipolar energy. When the monopolar shaft is in its advanced portion, the device's positive terminal is engaged with the generator's negative terminal and the device's negative terminal is disengaged from the generator, thereby allowing the generator to delivery monopolar energy to the device for delivery to tissue. A high impedance, e.g., substantially infinite and much greater than about 10 Ohms, detected by the generator is indicative of an open circuit state in which the device's positive terminal is engaged with the generator's negative terminal and the device's negative terminal is disengaged from the generator. In the open circuit state, the generator is configured to send current via its negative terminal, e.g., by inverting the current path, etc., to provide monopolar energy.

Figure 17:
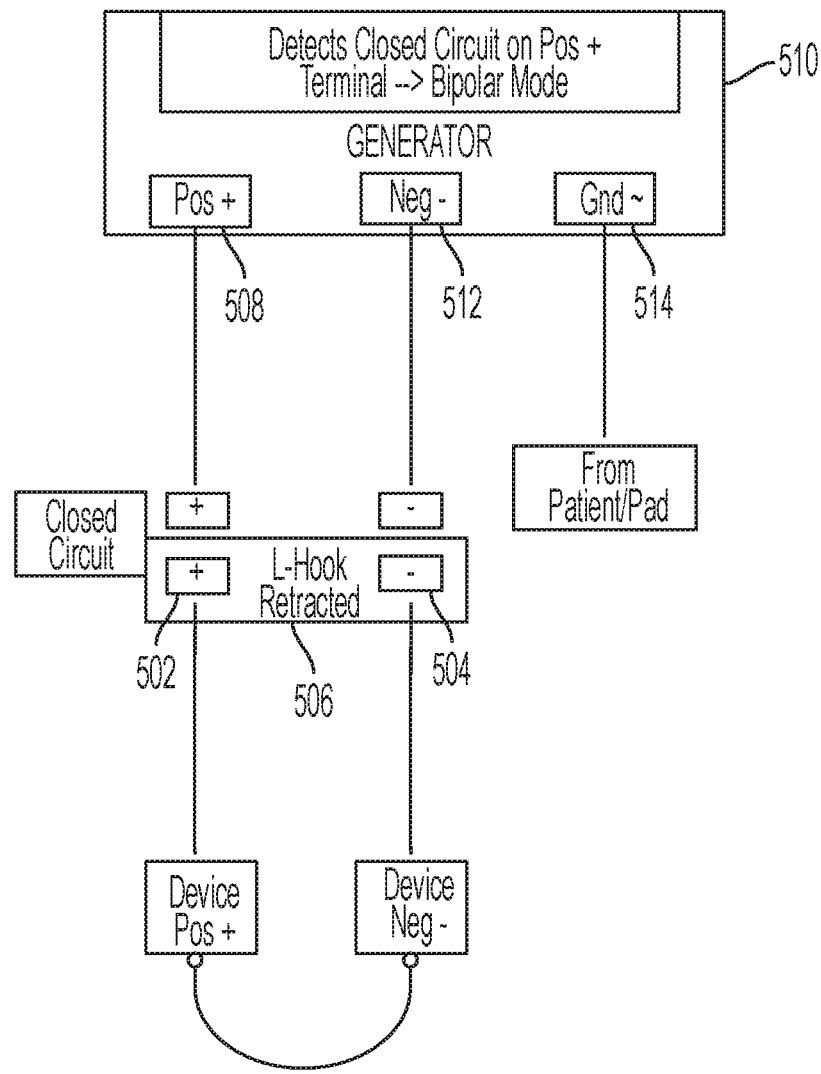
FIG. 17 is a schematic view of another embodiment of a portion of a surgical device operatively coupled with one embodiment of a generator.
Figure 18:
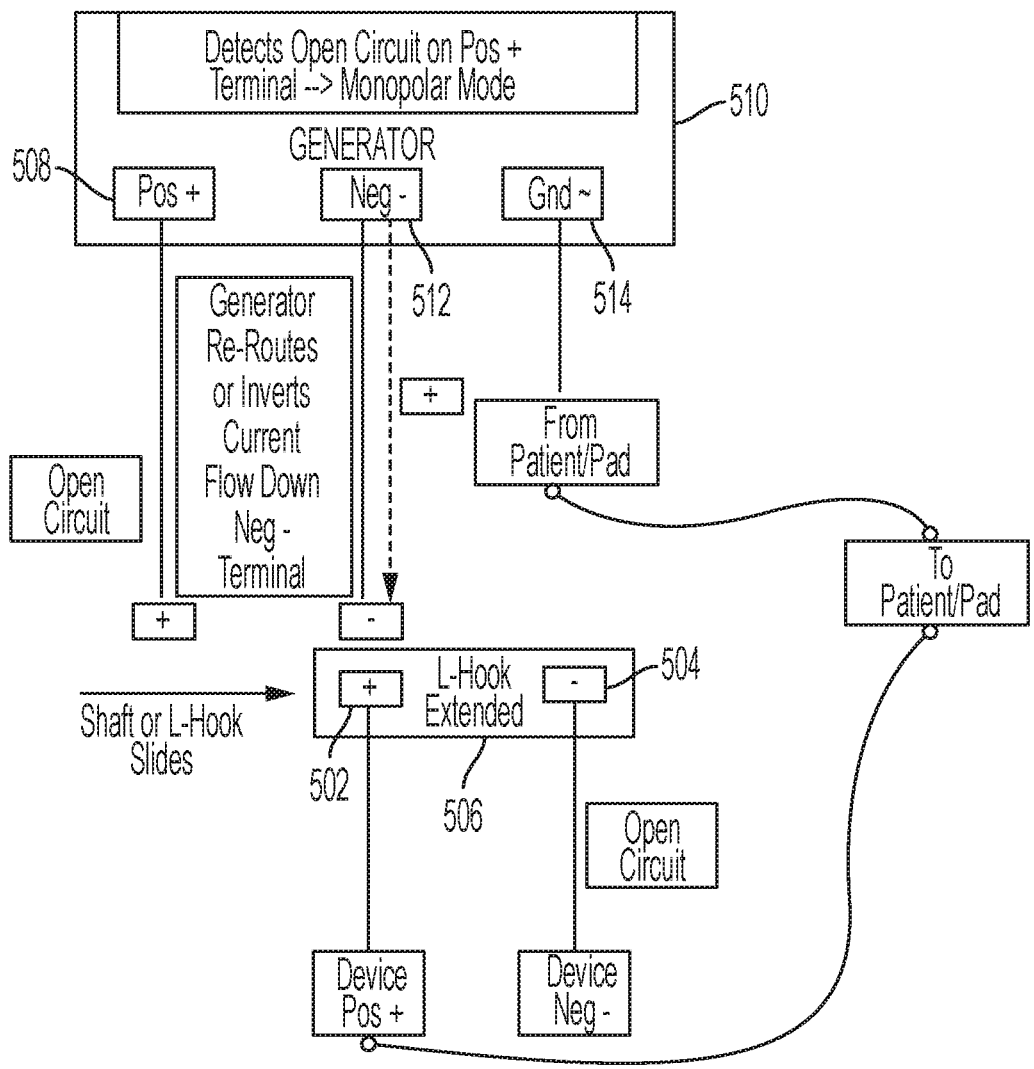
FIG. 18 is another schematic view of a portion of the surgical device operatively coupled with the generator.

FIGS. 17 and 18 illustrate one embodiment of a surgical device configured to switch between bipolar and monopolar modes and that includes a positive terminal or conductor 502 and a negative terminal or conductor 504 on a retractable monopolar shaft 506 of the device. The surgical device of FIGS. 17 and 18 is generally configured and used similar to the device 100 of FIG. 1 and includes a housing (not shown), an elongate shaft (not shown), an end effector (not shown) disposed at a distal end of the shaft, a stationary grip handle (not shown), a closure grip handle (not shown) that can use manual or powered components, a cutting or firing actuator (not shown), a movable knob (not shown), a sealing actuator (not shown), one or more electrical paths (not shown), a delivery or active electrode (not shown), a return electrode (not shown), the monopolar shaft 506, and a monopolar electrode (referred to as an "L-Hook" in FIGS. 17 and 18). In powered embodiments, the device can include a motor, a power source, and a processor.

FIG. 17 illustrates a bipolar mode of the device and shows a closed circuit state in which the device's positive terminal 502 is engaged with a positive terminal 508 of a generator 510, the device's negative terminal 504 is engaged with a negative terminal 512 of the generator 510, and a ground terminal 514 of the generator 510 is neutral and engaged with a ground 516 such as a patient or ground pad. FIG. 18 illustrates a monopolar mode of the device and shows an open circuit state in which the device's positive terminal 502 is engaged with the negative terminal 512 of the generator 510, the device's negative terminal 504 is disengaged from the generator, the generator's positive terminal 508 is disengaged from the device, and the ground terminal 514 of the generator 510 is engaged with the ground 516 and with the device's positive terminal 502 for energy return.

The device includes a movable knob (not shown) operatively coupled to the monopolar shaft 506 such that the longitudinal movement of the movable knob configured to move the device between bipolar and monopolar modes, as discussed above, causes movement of the monopolar shaft 506 and thus either causes the closed circuit state (knob in its first position) or the open circuit state (knob in its second position).

In other embodiments, instead of the surgical device's positive and negative terminals 502, 504 being on the device's monopolar shaft 506, the device's positive and negative terminals 502, 504 can be on the device's monopolar electrode.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An electrosurgical device, comprising:
    a housing;
    an elongate shaft extending from the housing and defining a longitudinal axis;
    an end effector coupled to a distal end of the elongate shaft, the end effector including first and second jaws, at least one of the first and second jaws being pivotable relative to the other from an open position, in which the first and second jaws are disposed in spaced relation relative to one another, to a clamping position, in which the first and second jaws cooperate to grasp tissue therebetween; and
    a knob configured to rotate relative to the housing to rotate the elongate shaft and end effector, the knob being configured to longitudinally translate between a first position, in which a pair of electrical contacts are aligned to complete a current path for a bipolar energy circuit allowing the first and second jaws to conduct energy through tissue grasped therebetween, and a second position, in which the pair of electrical contacts are offset to disrupt the current path for the bipolar energy circuit.

2. The device of claim 1, wherein, with the knob in the second position, an additional pair of electrical contacts is aligned to form a current path for a monopolar energy circuit allowing energy to be conducted through the end effector into tissue.

3. The device of claim 2, wherein the pair of electrical contacts includes a first electrical contact attached to an outer surface of the knob and a second electrical contact attached to an outer surface of the housing;
    the longitudinal translation of the knob is configured to cause the first electrical contact to longitudinally translate relative to the second electrical contact;
    the additional pair of electrical contacts includes a third electrical contact attached to an outer surface of the shaft and a fourth electrical contact attached to the outer surface of the housing; and
    the longitudinal translation of the knob is configured to cause the third electrical contact to longitudinally translate relative to the fourth electrical contact.

4. The device of claim 2, wherein the housing includes an upper portion substantially aligned with the longitudinal axis;
    the housing includes a lower portion with a handle; and
    the device further comprises a first actuation mechanism on the lower portion configured to activate energy delivery to the bipolar energy circuit, and a second actuation mechanism on the upper portion configured to activate energy delivery to the monopolar energy circuit.

5. The device of claim 4, wherein the handle includes a structure configured to require a user to grasp the device using a pistol grip for actuating the first actuation mechanism with an index finger, and to require a user to grasp the device using a pencil grip for actuating the second actuation mechanism using an index finger.

6. The device of claim 1, wherein the end effector includes a monopolar shaft having a distal tip positioned adjacent the first and second jaws; and
    with the knob in the second position, an additional pair of electrical contacts is aligned to form a current path for a monopolar energy circuit allowing energy to be conducted through the distal tip of the monopolar shaft and into tissue.

7. The device of claim 6, wherein distal longitudinal translation of the knob is configured to advance the monopolar shaft distally relative to the elongate shaft, and proximal longitudinal translation of the knob is configured to retract the monopolar shaft proximally relative to the elongate shaft.

8. The device of claim 1, wherein the housing includes a closure trigger configured to move relative to the housing to move at least one of the first and second jaws between the open position and the clamping position.

9. The device of claim 1, wherein:
    longitudinal translation of the knob is configured to move a switch carriage disposed within the housing between first and second positions;
    actuation of a button on the housing with the switch carriage in the first position is configured to activate energy delivery to the bipolar energy circuit; and
    actuation of the button on the housing with the switch carriage in the second position is configured to activate energy delivery to a monopolar energy circuit allowing energy to be conducted through the end effector into tissue.

10. The device of claim 9, wherein the switch carriage includes a first contact that aligns with the button when the switch carriage is in the first position; and
    the switch carriage includes a second contact that aligns with the button when the switch carriage is in the second position.

11. The device of claim 1, wherein the bipolar energy circuit includes a first positive conductor and a second negative conductor for allowing the first and second jaws to conduct energy through tissue grasped therebetween when the knob is in the first position; and
    one of the first and second conductors forms a monopolar energy circuit for allowing energy to be conducted through the end effector into tissue when the knob is in the second position.

12. The device of claim 11, further comprising a generator configured to detect whether the first positive conductor and the second negative conductor form a closed circuit for bipolar energy delivery or an open circuit for monopolar energy delivery.

13. The device of claim 12, wherein the generator being configured to detect whether the first positive conductor and the second negative conductor form the closed circuit for bipolar energy delivery or the open circuit for monopolar energy delivery includes the generator detecting an impedance;

a low detected impedance indicates that the first positive conductor and the second negative conductor form the closed circuit for bipolar energy; and a high detected impedance indicates that the first positive conductor and the second negative conductor form the open circuit for monopolar energy delivery.

14. An electrosurgical device, comprising:
a housing;
an elongate shaft extending from the housing and defining a longitudinal axis;
an end effector coupled to a distal end of the elongate shaft, the end effector being configured to deliver energy to tissue in contact with the end effector; and
a knob configured to rotate relative to the housing to rotate the elongate shaft and end effector, and the knob being configured to longitudinally translate in a proximal direction and in a distal direction to selectively switch the device between a bipolar mode, in which the energy is bipolar energy, and a monopolar mode, in which the energy is monopolar energy.

15. The device of claim 14, wherein longitudinal translation of the knob in the proximal direction is configured to cause a first pair of electrical contacts of the surgical device to be operatively connected such that bipolar energy is configured to be delivered to tissue in contact with the end effector; and
wherein longitudinal translation of the knob in the distal direction is configured to cause a second pair of electrical contacts of the surgical device to be operatively connected such that monopolar energy is configured to be delivered to tissue in contact with the end effector.

16. The device of claim 14, further comprising a monopolar energy delivery shaft configured to deliver the monopolar energy, to be advanced distally in response to switching the device from the bipolar mode to the monopolar mode, and to be retracted proximally in response to switching the device from the monopolar mode to the bipolar mode;
wherein the end effector includes a first jaw with a delivery electrode for delivery of the bipolar energy, and the end effector includes a second jaw with a return electrode for return of the bipolar energy.

17. The device of claim 16, wherein the monopolar energy delivery shaft includes a distal hook member.

18. The device of claim 14, further comprising a positive conductor and a negative conductor;
wherein in the bipolar mode the positive conductor of the device is configured to be operatively connected to a positive conductor of a generator and the negative conductor of the device is configured to be operatively connected to a negative conductor of the generator to allow the generator to deliver energy to the device via the operatively connected positive conductors and to receive energy from the device via the operatively connected negative conductors; and
wherein in the monopolar mode the negative conductor of the device is configured to be operatively connected to the positive conductor of the generator to allow the generator to deliver energy to the device via the operatively connected negative conductor of the device and positive conductor of the generator.

19. A surgical method, comprising:
positioning an end effector of a surgical device in contact with tissue, the end effector being coupled to a distal end of an elongate shaft of the surgical device;

rotating a knob of the surgical device to rotate the end effector and the elongate shaft;
longitudinally translating the knob in a first direction and thereby causing a pair of electrical contacts of the surgical device to be aligned to complete a current path for a bipolar energy circuit allowing the end effector to conduct energy through the tissue in contact with the end effector; and
longitudinally translating the knob in a second direction, which is opposite to the first direction, and thereby causing the pair of electrical contacts of the surgical device to be offset to disrupt the current path.

20. The method of claim 19, further comprising:
with the current path completed, causing energy to be conducted through the tissue in contact with the end effector using the pair of electrical contacts; and
with the current path disrupted, causing energy to be conducted through the tissue in contact with the end effector using another pair of electrical contacts of the surgical device.

21. The method of claim 20, wherein:
longitudinally translating the knob in the first direction causes a switch carriage of the surgical device to be in a first position relative to an actuator of the surgical device;
causing energy to be conducted with the current path completed includes actuating the actuator;
longitudinally translating the knob in the second direction causes the switch carriage to be in a second position relative to the actuator; and
causing energy to be conducted with the current path disrupted includes actuating the actuator.

22. The method of claim 20, wherein:
causing energy to be conducted with the current path completed includes actuating a first actuator of the surgical device; and
causing energy to be conducted with the current path disrupted includes actuating a second actuator of the surgical device.

23. The method of claim 19, wherein:
with the pair of electrical contacts aligned:
a positive conductor of the surgical device is operatively connected to a positive conductor of a generator,
a negative conductor of the surgical device is operatively connected to a negative conductor of the generator, and
the method further comprises causing the generator to deliver energy to the surgical device via the positive conductors of the surgical device and the generator; and
with the pair of electrical contacts offset:
the positive conductor of the surgical device is disconnected from the positive conductor of the generator,
the negative conductor of the surgical device is operatively connected to the positive conductor of the surgical device, and
the method further comprises causing the generator to deliver energy to the surgical device via the negative conductor of the surgical device and the positive conductor of the generator.

* * * * *